United States Patent [19]

Matassa et al.

[11] Patent Number: 5,510,362
[45] Date of Patent: Apr. 23, 1996

[54] IMIDAZOLE, TRIAZOLE AND TETRAZOLE DERIVATIVES

[75] Inventors: Victor G. Matassa, Furneux Pelham; Austin J. Reeve, Great Dunmow; Francine Sternfeld, London; Helen Routledge, Chester-Le-Street; Leslie Street, Harlow, all of United Kingdom

[73] Assignee: Merck, Sharp and Dohme Limited, Hoddesdon, England

[21] Appl. No.: 295,884

[22] PCT Filed: Mar. 5, 1993

[86] PCT No.: PCT/GB93/00474

§ 371 Date: Sep. 8, 1994

§ 102(e) Date: Sep. 8, 1994

[87] PCT Pub. No.: WO93/18029

PCT Pub. Date: Sep. 16, 1993

[30] Foreign Application Priority Data

Mar. 13, 1992 [GB] United Kingdom .................. 9205482
Jul. 24, 1992 [GB] United Kingdom .................. 9215731

[51] Int. Cl.$^6$ ..................... A61K 31/41; C07D 403/14
[52] U.S. Cl. ..................... 514/381; 514/383; 514/397; 514/414; 548/256; 548/266.4; 548/312.1; 548/466
[58] Field of Search ..................... 514/381, 383, 514/397, 414; 548/256, 266.4, 312.1, 466

[56] References Cited

FOREIGN PATENT DOCUMENTS

0313397A1 4/1989 European Pat. Off. .
0497512A2 8/1992 European Pat. Off. .
WO91/18897 12/1991 WIPO .

Primary Examiner—Jacqueline Haley
Attorney, Agent, or Firm—Robert J. North; Melvin Winokur

[57] ABSTRACT

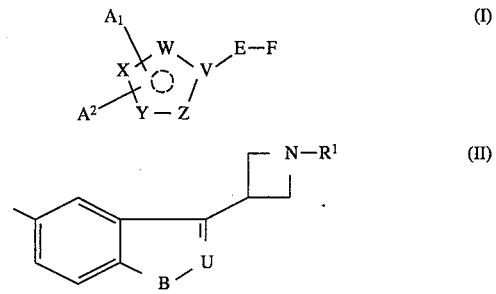

A class of substituted imidazole, triazole and tetrazole derivatives of formula (I), wherein the broken circle represents two non-adjacent double bonds in any position in the five-membered ring; two, three or four of V,W,X,Y and Z represent nitrogen and the remainder represent carbon provided that, when two of V,W,X,Y and Z represent nitrogen and the remainder represent carbon, then the said nitrogen atoms are in non-adjacent positions within the five-membered ring; E represents a bond or a straight or branched alkylene chain containing from 1 to 4 carbon atoms; F represents a group of formula (II); U represents nitrogen or C—$R^2$; B represents oxygen, sulphur or N—$R^3$; are selective agonists of 5—$HT_1$-like receptors and are therefore useful in the treatment of clinical conditions, in particular migraine and associated disorders, for which a selective agonist of these receptors is indicated.

8 Claims, No Drawings

IMIDAZOLE, TRIAZOLE AND TETRAZOLE DERIVATIVES

This application is a National Stage application of PCT/GB93/00474 filed Mar. 5, 1993 which published as WO/93/18029 on Sep. 16, 1993.

The present invention relates to a class of substituted imidazole, triazole and tetrazole derivatives which act on 5-hydroxytryptamine (5—HT) receptors, being selective agonists of so-called "5—$HT_1$-like" receptors. They are therefore useful in the treatment of clinical conditions for which a selective agonist of these receptors is indicated.

5—$HT_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5—$HT_1$-like receptor agonists, are accordingly of particular use in the treatment of migraine and associated conditions, e.g. cluster headache, chronic paroxysmal hemicrania, headache associated with vascular disorders, tension headache and paediatric migraine.

EP-A-0313397 and WO-A-91/18897 describe separate classes of tryptamine derivatives substituted by various five-membered heteroaliphatic rings, which are stated to be specific to a particular type of "5—$HT_1$-like" receptor and thus to be effective therapeutic agents for the treatment of clinical conditions, particularly migraine, requiring this activity. However, neither EP-A-0313397 nor WO-A-91/18897 discloses or suggests the imidazole, triazole and tetrazole derivatives provided by the present invention.

EP-A-0497512, published on 5th Aug. 1992, describes a class of substituted imidazole, triazole and tetrazole derivatives which are stated to be selective agonists of 5—$HT_1$-like receptors and hence to be of particular use in the treatment of migraine and associated conditions.

The present invention provides a compound of formula I, or a salt or prodrug thereof:

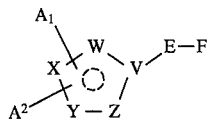

(I)

wherein the broken circle represents two non-adjacent double bonds in any position in the five-membered ring;

two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring;

$A^1$ represents hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$;

$A^2$ represents a non-bonded electron pair when four of V, W, X, Y and Z represent nitrogen and the other represents carbon; or, when two or three of V, W, X, Y and Z represent nitrogen and the remainder represent carbon, $A^2$ represents hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$;

E represents a bond or a straight or branched alkylene chain containing from 1 to 4 carbon atoms;

F represents a group of formula

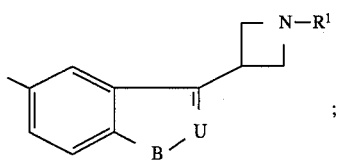

;

U represents nitrogen or C—$R^2$;
B represents oxygen, sulphur or N—$R^3$;
$R^1$, $R^2$ and $R^3$ independently represent hydrogen or $C_{1-6}$ alkyl;
$R^x$ and $R^y$ independently represent hydrogen, hydrocarbon or a heterocyclic group, or $R^x$ and $R^y$ together represent a $C_{2-6}$ alkylene group;
$R^z$ represents hydrogen, hydrocarbon or a heterocyclic group;
T represents oxygen, sulphur or a group of formula =N.G; and
G represents hydrocarbon, a heterocyclic group or an electron-withdrawing group.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

A particular aryl group is phenyl.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and. morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{1-3}$ alkoxycarbonyl ($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl ($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, $-COR^x$, $-CO_2R^x$ or $-SO_2R^x$, in which $R^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

It will be appreciated that the imidazole, triazole and tetrazole rings of formula I can exist in a variety of isomeric forms having differing substitution patterns. These may suitably be represented by formulae IA to IT as follows:

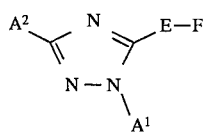 (IA)

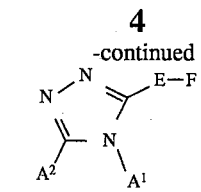 (IB)

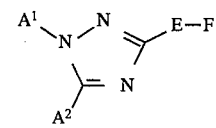 (IC)

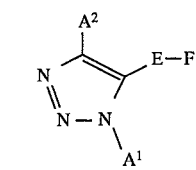 (ID)

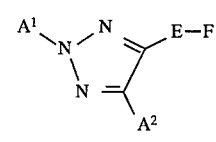 (IE)

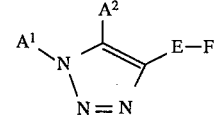 (IF)

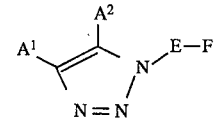 (IG)

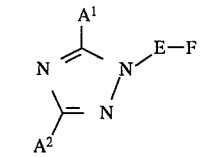 (IH)

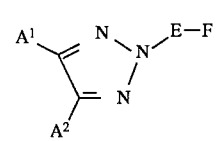 (IJ)

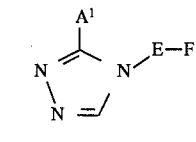 (IK)

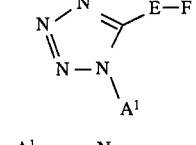 (IL)

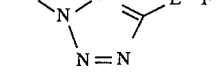 (IM)

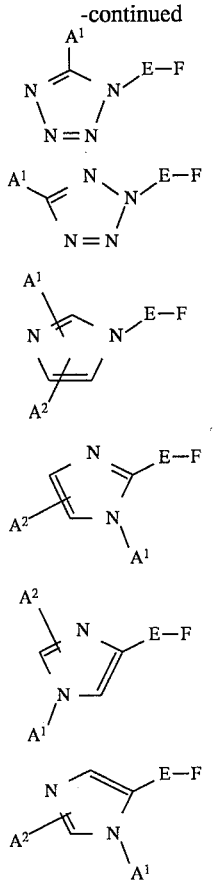

wherein $A^1$, $A^2$, E and F are as defined above. Preferred imidazole, triazole and tetrazole rings of formula I include the rings represented by formulae IA, IC, IG, IH, IK, IL, IN and IQ above, especially IH and IK.

The alkylene chain E may be, for example, methylene, ethylene, 1-methylethylene, propylene or 2-methylpropylene. Alternatively, the group E may represent a single bond such that the group F in formula I is attached directly to the five-membered heteroaromatic ring.

The group F is suitably an indole, benzofuran or benzthiophene moiety of formula FA, or an indazole moiety of formula FB:

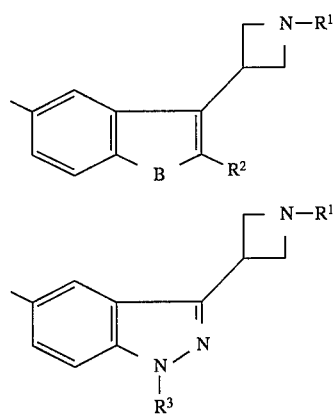

wherein B, , $R^1$, $R^2$ and $R^3$ are as defined above. Preferably, the group F represents an indole moiety of structure FC:

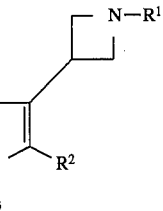

wherein $R^1$, $R^2$ and $R^3$ are as defined above, in particular wherein $R^2$ and $R^3$ are both hydrogen.

It will be appreciated that when four of V, W, X, Y and Z represent nitrogen and the other represents carbon, i.e. when the ring of formula I is a tetrazole ring, then the group $A^2$ will be a non-bonded electron pair. Otherwise, $A^1$ and $A^2$ will independently represent hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^xCTNR^xR^y$.

Suitable values for the groups $A^1$ and/or $A^2$ include $C_{1-6}$ alkyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy or $C_{1-6}$ alkylthio, any of which groups may be optionally substituted; and hydrogen, halogen, cyano, trifluoromethyl or —$NR^xR^y$, in which $R^x$ and $R^y$ are as defined above. Examples of optional substituents on the groups $A^1$ and/or $A^2$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$ and/or $A^2$ include hydrogen, methyl, methoxymethyl, aminomethyl, dimethylaminomethyl, acetylaminomethyl, benzoylaminomethyl, t-butoxycarbonylaminomethYl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylamino-ethylamino and methylsulphonylaminoethylamino.

Preferred values of $A^1$ and/or $A^2$ include hydrogen, methyl, ethyl and amino.

Preferred values for the groups $R^1$, $R^2$ and $R^3$ include hydrogen and methyl.

A particular sub-class of compounds according to the invention is represented by the compounds of formula IIA, and salts and prodrugs thereof:

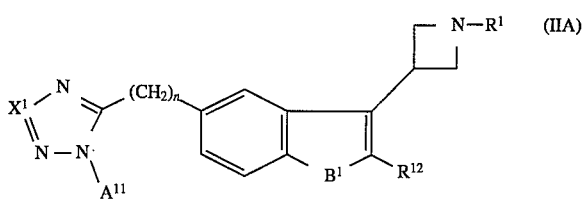

wherein $X^1$ represents nitrogen or $A^{12}$—C;

n is zero, 1, 2 or 3;

$B^1$ represents oxygen, sulphur or N—$R^{13}$;

$A^{11}$ and $A^{12}$ independently represent $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$) alkylamino, any of which groups may be optionally substituted; or hydrogen, halogen, cyano, trifluoromethyl or amino; and $R^{11}$, $R^{12}$ and $R^{13}$ independently represent hydrogen or $C_{1-6}$ alkyl.

Examples of optional substituents on the groups $A^{11}$ and $A^{12}$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^{11}$ and $A^{12}$ with respect to formula IIA include hydrogen, methyl, ethyl and amino. When $X^1$ represents $A^{12}$—C, the group $A^{11}$ is preferably hydrogen or methyl.

Preferably, $R^{12}$ and $R^{13}$ each represents hydrogen. Preferred values of $R^{11}$ with respect to formula IIA include hydrogen and methyl.

Another sub-class of compounds according to the invention is represented by the compounds of formula IIB, and salts and prodrugs thereof:

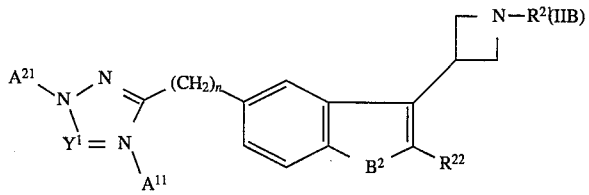

wherein $Y^1$ represents nitrogen or $A^{22}$—C;

n is zero, 1, 2 or 3;

$B^2$ represents oxygen, sulphur or N—$R^{23}$;

$A^{21}$ and $A^{22}$ independently represent $C_{1-6}$ alkyl, $C_{2-6}$ alkenyl, $C_{2-6}$ alkynyl, $C_{3-7}$ cycloalkyl, aryl, aryl ($C_{1-6}$) alkyl, $C_{1-6}$ heterocycloalkyl, heteroaryl, heteroaryl ($C_{1-6}$) alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{21}$, $R^{22}$ and $R^{23}$ independently represent hydrogen or $C_{1-6}$ alkyl.

Examples of optional substituents on the groups $A^{21}$ and $A^{22}$ correspond to those indicated for the groups $A^{11}$ and $A^{12}$ with respect to formula IIA above. Particular values of $A^{21}$ and $A^{22}$ with respect to formula IIB include hydrogen, methyl and ethyl.

Preferably, $R^{22}$ and $R^{23}$ each represents hydrogen. Preferred values of $R^{21}$ with respect to formula IIB include hydrogen and methyl.

A further sub-class of compounds according to the invention is represented by the compounds of formula IIC, and salts and prodrugs thereof:

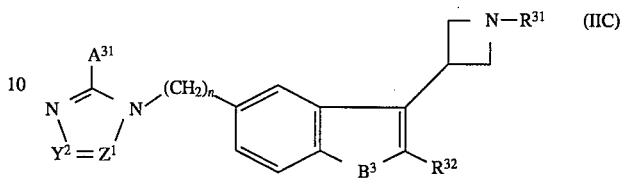

wherein $Y^2$ represents nitrogen or $A^{32}$—C;

$Z^1$ represents nitrogen or CH;

n is zero, 1, 2 or 3;

$B^3$ represents oxygen, sulphur or N—$R^{33}$;

$A^{31}$ and $A^{32}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{31}$, $R^{32}$ and $R^{33}$ independently represent hydrogen or $C_{1-6}$ alkyl.

Examples of optional substituents on the groups $A^{31}$ and $A^{33}$ correspond to those indicated for the groups $A^{11}$ and $A^{12}$ with respect to formula IIA above. Particular values of $A^{31}$ and $A^{32}$ with respect to formula IIC include hydrogen, methyl and amino.

Preferably, $R^{32}$ and $R^{33}$ each represents hydrogen. Preferred values of $R^{31}$ include hydrogen and methyl.

A still further sub-class of compounds according to the invention is represented by the compounds of formula IID, and salts and prodrugs thereof:

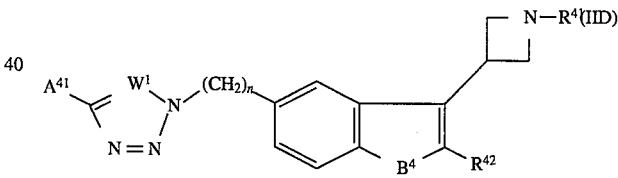

wherein $W^1$ represents nitrogen or C—$A^{42}$;

n is zero, 1, 2 or 3;

$B^4$ represents oxygen, sulphur or N—$R^{43}$;

$A^{41}$ and $A^{42}$ independently represent $C_{1-6}$ alkyl, $C_{2-6}$ alkenyl, $C_{2-6}$ alkynyl, $C_{3-7}$ cycloalkyl, aryl, aryl ($C_{1-6}$) alkyl, $C_{3-7}$ heterocycloalkyl, heteroaryl, heteroaryl ($C_{1-6}$) alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{41}$, $R^{42}$ and $R^{43}$ independently represent hydrogen or $C_{1-6}$ alkyl.

Examples of optional substituents on the groups $A^{41}$ and $A^{42}$ correspond to those indicated for the groups $A^{11}$ and $A^{12}$ with respect to formula IIA above. Particular values of $A^{41}$ and $A^{42}$ with respect to formula IID include hydrogen and methyl.

Preferably, $R^{42}$, and $R^{43}$ each represents hydrogen. Preferred values of $R^{41}$ include hydrogen and methyl.

Specific compounds within the scope of the present invention include:

N-methyl-3-[5-(2-methylimidazol-1-ylmethyl)-1H-indol-3-yl]azetidine;

N-methyl-3-[5-(1-methyltetrazol-5-ylmethyl)-1H-indol-3yl-] azetidine;
N-methyl-3-[5-(1,2,4-triazol-1-yl)-1H-indol-3yl] azetidine;
N-methyl-3-[5-(imidazol-1-yl)-1H-indol-3-yl-]azetidine;
N-methyl-3-[5-(2-(1-methyltetrazol-5-yl)ethyl)-1H-indol-3-yl]azetidine;
N-methyl-3-[5-(1,2,4-triazol-1-ylmethyl)-1H-indol-3yl] azetidine:
N-methyl-3-[5-(1,2,4-triazol-4-yl)-1H-indol-3yl] azetidine;
N-methyl-3-[5-(imidazol-1-ylmethyl)-1H-indol-3yl] azetidine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The 1,2,4-triazole compounds of this invention may be prepared by a process which comprises reacting a reactive derivative of a carboxylic acid of formula $R^a$—$CO_2H$ with a compound either of formula III or of formula IV, or a salt thereof:

(III)

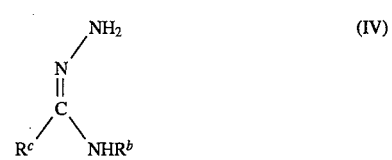

(IV)

wherein one of $R^a$, $R^b$ and $R^c$ is a group of formula $A^1$, another is a group of formula $A^2$, and the third is a group of formula —E—F, as defined with reference to formula I above.

Suitable reactive derivatives of the acid $R^a$—$CO_2H$ include esters, for example $C_{1-4}$ alkyl esters; thioesters, for example pyridylthioesters; acid anhydrides, for example $(R^a$—$CO)_2O$; acid halides, for example acid chlorides; orthoesters; and primary, secondary and tertiary amides.

A preferred reactive derivative of the acid $R^a$—$CO_2H$ is the iminoether derivative of formula V:

(V)

where R is $C_{1-4}$ alkyl.

The reagent of formula III may be generated in situ in the reaction mixture. For example, the reaction may be effected by treating a compound of formula V above with an alkyl hydrazine, e.g. methyl hydrazine, followed by a suitable carboxylic acid such as formic acid.

The reaction is conveniently carried out by heating the reagents together, optionally in a solvent, for example tetrahydrofuran, dimethylformamide or a lower alkanol such as ethanol, propanol or isopropanol, at about 20° C. to 100° C. for about 1 to 6 hours.

Where $R^a$ is a group of formula —E—F and the group F is an indole moiety of structure FC as defined above, the reactive derivative of a carboxylic acid of formula $HO_2C$—E—F may be prepared by reacting a compound of formula VI:

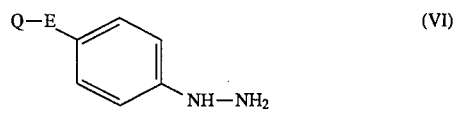

(VI)

wherein Q represents a reactive carboxylate moiety, and E is as defined above; with a compound of formula VII or a carbonyl-protected form thereof:

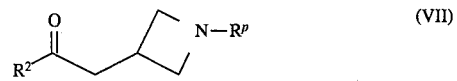

(VII)

wherein $R^2$ is as defined above and $R^p$ represents an amino-protecting group; followed by removal of the protecting group $R^p$; and subsequently, where required, N-alkylation by standard methods to introduce the moieties $R^1$ and/or $R^3$.

Suitable carbonyl-protected forms of the compounds of formula VII include the dimethyl acetal or ketal derivatives.

Suitable examples of amino-protecting groups for the substituent $R^p$ include carboxylic acid groups such as chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, p-methoxybenzyl, trityl, o-nitrophenylsulphenyl or benzylidene.

Preferred amino-protecting groups include t-butoxycarbonyl, benzyloxycarbonyl and p-methoxybenzyl.

The removal of the protecting group present in the resultant compound may be effected by an appropriate procedure depending upon the nature of the protecting group. Typical procedures include hydrogenation in the presence of a palladium catalyst (e.g. palladium carbon or palladium black) for benzyloxycarbonyl, p-nitrobenzyloxycarbonyl, p-bromobenzyloxycarbonyl, p-phenylazobenzyloxycarbonyl, p-(p,-methoxyphenylazo)benzyloxycarbonyl and trityl groups; treatment with hydrogen bromide in glacial acetic acid or trifluoroacetic acid for benzyloxycarbonyl, p-bromobenzyloxycarbonyl, p-phenylazobenzyloxycarbonyl and t-butoxycarbonyl groups; treatment with acetic acid and/or a mineral acid such as hydrochloric acid or sulphuric acid for trityl, t-butoxycarbonyl, formyl and benzylidene groups; and treatment with 2,3-dichloro-5,6-dicyano-1,4-benzoquinone for p-methoxybenzyl groups.

The reaction of compounds VI and VII may be carried out in a single step (Fischer indole synthesis) or by an initial non-cyclising step at a lower temperature to give a compound of formula VIII:

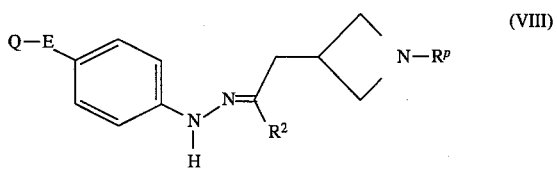
(VIII)

wherein Q, E, $R^2$ and $R^p$ are as defined above; followed by cyclisation using a suitable reagent, such as a polyphosphate ester, to give a compound of formula Q-E-F.

The hydrazines of formula VI may be prepared from the corresponding anilines of formula IX:

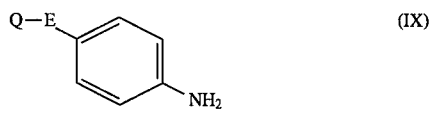
(IX)

wherein Q and E are as defined above; by diazotisation followed by reduction. Diazotisation is typically carried out using sodium nitrite/conc. HCl and the resulting diazo product reduced in situ using, for example, tin(II) chloride/conc. HCl sodium sulphite/conc. HCl, or sodium sulphite/conc. $H_2SO_4$.

The anilines of formula IX may be prepared by reduction of the corresponding nitro compounds of formula X:

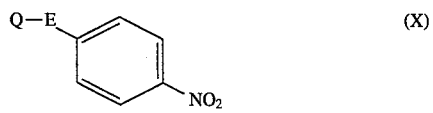
(X)

wherein Q and E are as defined above; typically by transfer hydrogenation using a hydrogenation catalyst such as palladium on charcoal in the presence of a hydrogen donor such as ammonium formate, or alternatively by conventional catalytic hydrogenation or using tin(II) chloride.

Where they are not commercially available, the nitro compounds of formula X may be synthesised by standard methods well known to those skilled in the art.

Where $R^a$ is a group of formula —E—F and the group F is an indazole moiety of structure FB as defined above, the reactive derivative of a carboxylic acid of formula $HO_2C$—E—F may be prepared by the cyclisation of a compound of formula XI:

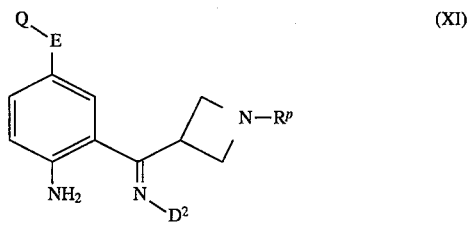
(XI)

wherein Q, E and Rp are as defined above; and $D^2$ represents a readily displaceable group; followed by removal of the protecting group $R^p$; and subsequently, where required, N-alkylation by standard methods to introduce the moieties $R^1$ and/or $R^3$.

The cyclisation of compound XI is conveniently achieved in a suitable organic solvent at an elevated temperature, for example in a mixture of m-xylene and 2,6-lutidine at a temperature in the region of 140° C.

The readily displaceable group $D^2$ in the compounds of formula XI suitably represents a $C_{1-4}$ alkanoyloxy group, preferably acetoxy. Where $D^2$ in the desired compound of formula XI represents acetoxy, this compound may be conveniently prepared by treating a carbonyl compound of formula XII:

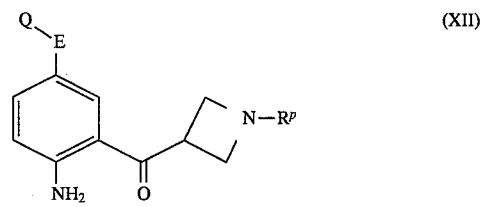
(XII)

wherein Q, E and $R^p$ are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XII may be conveniently prepared by ozonolysis of an indole derivative of formula XIII:

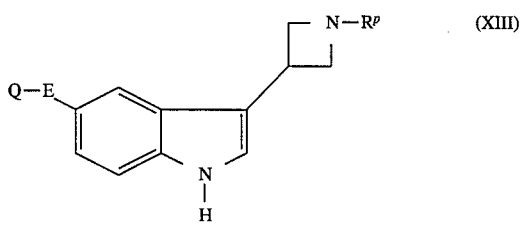
(XIII)

wherein Q, E and $R^p$ are as defined above; followed by a reductive work-up, advantageously using dimethylsulphide.

The indole derivative of formula XIII may be prepared by methods analogous to those described in the accompanying Examples, or by procedures well known from the art.

In an alternative process, the triazole compounds according to the invention may be prepared by a method which comprises reacting a compound of formula XIV:

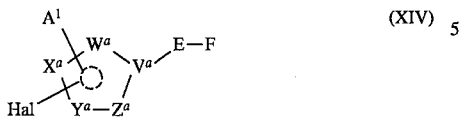

wherein $A^1$, E and F are as defined above, Hal represents halogen, and two of $V^a$, $W^a$, $X^a$, $Y^a$ and $Z^a$, to one of which the group Hal is attached, represent carbon and the remainder represent nitrogen; with a reagent which provides an anion $^-A^2$, where $A^2$ is as previously defined.

Reagents which may provide the anion $^-A^2$ include Grignard reagents $A^2$MgHal (where Hal=halogen); organocuprate reagents such as $LiA_2^2Cu$; organolithium reagents $A^2Li$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

The 1,2,3-triazole compounds according to the present invention may be prepared by a process which comprises the cycloaddition of an alkyne of formula $R^a$—C≡C—$R^b$ with an azide of formula $R^c$—$N_3$, where $R^a$, $R^b$ and $R^c$ are as defined above.

The cycloaddition reaction may be conveniently effected in a suitable solvent such as tetrahydrofuran, ideally by heating in an autoclave for 8 hours.

The tetrazole compounds in accordance with the invention may be prepared by a process which comprises the cycloaddition of a nitrile of formula N≡C—$R^d$ with an azide of formula $R^e$—$N_3$, where one of $R^d$ and $R^e$ represents a group of formula $A^1$ and the other is a group of formula —E—F, as defined previously. 10 The cycloaddition reaction is conveniently effected by heating the reactants together at an elevated temperature, e.g. a temperature in the region of 150° C., in a suitable solvent such as N-methylpyrrolid-2-one, advantageously in the presence of triethylamine hydrochloride. The product obtained from the cycloaddition reaction will generally be a mixture of isomers substituted by the $A^1$ group at positions 1 and 2 of the tetrazole ring, corresponding to structures IL and IM respectively as defined above. These isomers may conveniently be separated using conventional techniques such as chromatography.

In an alternative process, the tetrazole compounds of the invention may be prepared by a method which comprises reacting a compound of formula $R^e$—L with a tetrazole derivative of formula XV:

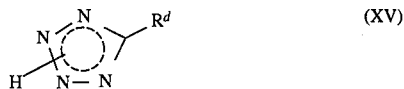

wherein one of $R^d$ and $R^e$ represents a group of formula $A^1$ and the other is a group of formula —E—F, as defined above, and L represents a suitable leaving group; in the presence of a base such as triethylamine.

The leaving group L suitably represents halogen, e.g. bromine or iodine, or a sulphonate derivative such as tosylate or mesylate.

The reaction is conveniently carried out in a suitable organic solvent, e.g. acetonitrile, at room temperature.

The tetrazole derivatives of formula XV may be prepared by cycloaddition of a nitrile of formula N≡C—$R^d$ with sodium azide, advantageously under the conditions described above for the reaction between the nitrile N≡C—$R^d$ and the azide $R^e$—$N_3$; followed by acidification with a mineral acid such as hydrochloric acid.

In a further process, the compounds according to the invention wherein the group F is an indole moiety of structure FC as defined above may be prepared by a method which comprises reacting a compound of formula XVI:

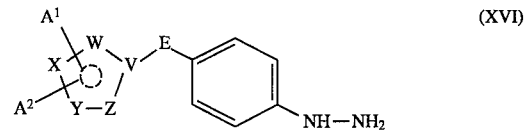

wherein V, W, X, Y, Z, $A^1$, $A^2$ and E are as defined above; with a compound of formula VII as defined above, or a carbonyl-protected form thereof, e.g. the dimethyl acetal or ketal; followed by removal of the protecting group $R^p$; and subsequently, where required, N-alkylation by standard methods to introduce the moieties $R^1$ and/or $R^3$.

As with that between compounds VI and VII, the reaction between compounds XVI and VII may be carried out in a single step (Fischer indole synthesis) or by an initial non-cyclising step at a lower temperature to give a compound of formula XVII:

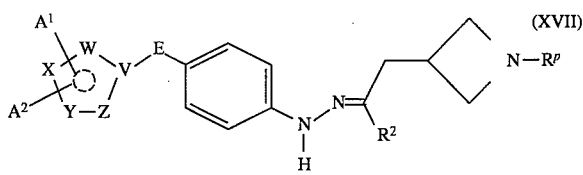

wherein V, W, X, Y, Z, $A^1$, $A^2$, E, $R^2$ and $R^p$ are as defined above; followed by cyclisation using a suitable reagent, e.g. a polyphosphate ester.

The hydrazines of formula XVI may be prepared from the corresponding anilines of formula XVIII:

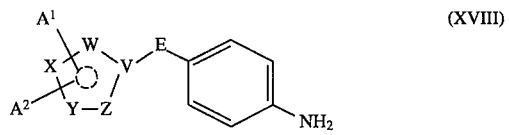

wherein V, W, X, Y, Z, $A^1$ $A^2$ and E are as defined above; , by methods analogous to those described above with reference to the compounds of formula IX.

The anilines of formula XVIII may be prepared from the corresponding nitro compounds of formula XIX:

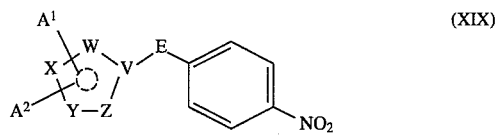

wherein V, W, X, Y, Z, $A^1$, $A^2$ and E are as defined above; by methods analogous to those described above with reference to the compounds of formula X.

The nitro compounds of formula XIX may be prepared by a variety of methods which will be readily apparent to those skilled in the art. For example, where V represents a nitrogen atom, the relevant compounds of formula XIX may be prepared by reacting the anion of a compound of formula XX with a compound of formula XXI:

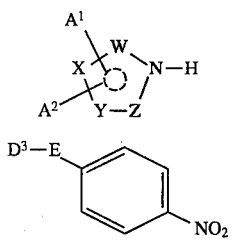 (XX)

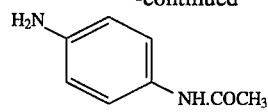 (XXI)

wherein W, X, Y, Z, $A^1$, $A^2$ and E are as defined above, and $D^3$ represents a readily displaceable group.

Where compound XX is a triazole or tetrazole derivative, the anion thereof may be generated by carrying out the reaction in a base such as triethylamine. Where compound XX is an imidazole derivative, the anion thereof may conveniently be generated if the reaction is carried out in the presence of sodium hydride using N,N-dimethylformamide as solvent. Where salts of the compounds of formula XX are commercially available, e.g. the sodium salt of 1,2,4-triazole, these are advantageously utilised in N,N-dimethylformamide solution in place of the compounds of formula XX themselves, with no requirement in this instance for additional base to be present in the reaction mixture.

The readily displaceable group $D^3$ in the compounds of formula XXI is suitably a halogen atom, preferably bromine; except when the moiety $D^3$ is attached directly to the aromatic ring, i.e. when E represents a bond, in which case $D^3$ is preferably fluorine.

In an alternative approach, the compounds of formula XIX wherein the five-membered heteroaromatic ring is a 1,2,4-triazol-1-yl moiety and $A^1$ and $A^2$ are both hydrogen may be prepared by reacting 4-amino-1,2,4-triazole with a compound of formula XXI as defined above, followed by deamination of the resulting 1-substituted 4-amino- 4H-1,2,4-triazolium salt by treatment with nitrous acid and subsequent neutralisation. This transformation, which may be accomplished in two separate steps or advantageously as a "one-pot" procedure with both steps combined, is conveniently effected using reaction conditions analogous to those described in *J. Org. Chem.*, 1989, 54, 731.

Where they are not commercially available, the nitro compounds of formula XXI above may be prepared by procedures analogous to those described in the accompanying Examples, or by methods well known from the art.

In an alternative approach to the 1,2,4-triazole derivatives, the nitro compounds of formula XIX may be prepared from those of formula X above by appropriate modification of the moiety Q using, for example, methods analogous to those described above with reference to the compounds of formulae III and IV. Thus, for example, since Q in the compounds of formula X represents a reactive carboxylate moiety, the compounds of formula XIX may be prepared therefrom by reaction with a compound of formula $A^2$—C(═NNH$A^1$)NH$_2$ or $A^2$—C(═NNH$_2$)NH$A^1$.

Following a further representative pathway, the 10 aniline derivatives of formula XVIII wherein the five-membered heteroaromatic ring is a 1,2,4-triazol-4-yl moiety, E is a bond and $A^1$ and $A^2$ are both hydrogen may be prepared by reacting the hydrazine derivative of formula XXII with the acetanilide of formula XXIII:

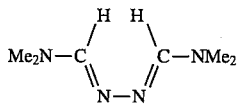 (XXII)

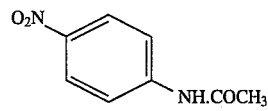 (XXIII)

followed by removal of the N-acetyl protecting group.

The reaction between compounds XXII and XXIII is conveniently effected in refluxing toluene, advantageously in the presence of a catalytic quantity of p-toluenesulphonic acid. Subsequent removal of the N-acetyl protecting group is typically effected in hot aqueous 5N hydrochloric acid.

The hydrazine derivative of formula XXII can be prepared from N,N'-diformylhydrazine by reaction with thionyl chloride/N,N-dimethylformamide, as reported in *J. Chem. Soc. (C)*, 1967, 1664, and subsequent treatment with sodium methoxide in methanol.

The acetanilide of formula XXIII may be prepared by reduction of the corresponding nitro compound of formula XXIV:

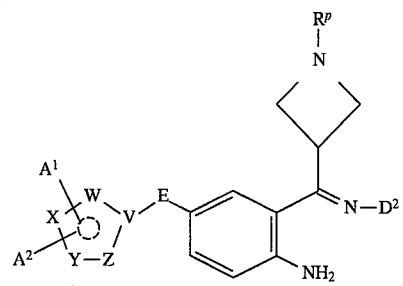 (XXIV)

typically by transfer hydrogenation using a hydrogenation catalyst in the presence of a hydrogen donor such as ammonium formate, or alternatively by conventional catalytic hydrogenation or using tin(II) chloride.

The nitro compound of formula XXIV is commercially available from the Aldrich Chemical Company Ltd., Gillingham, United Kingdom.

In a still further process, the compounds according to the invention wherein the group F is an indazole moiety of structure FB as defined above may be prepared by a method which comprises cyclising a compound of formula XXV:

(XXV)

wherein V, W, X, Y, Z, $A^1$, $A^2$, E, $R^p$ and $D^2$ are defined above; followed by removal of the protecting group $R^pp$; and subsequently, where required, N-alkylation by standard methods to introduce the moieties $R^1$ and/or $R^3$.

As with the cyclisation of compound XI, that of compound XXV is conveniently achieved in a suitable organic solvent at an elevated temperature, for example in a mixture of m-xylene and 2,6-lutidine at a temperature in the region of 140° C.

The compounds of formula XXV may, for example, be prepared from the corresponding compound of formula XXVI:

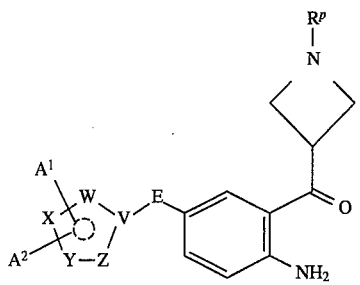

(XXVI)

wherein V, W, X, Y, Z, A¹, A², E and R$^p$ are as defined above; or a protected derivative thereof; which in turn may be prepared from the corresponding compound of formula XXVII:

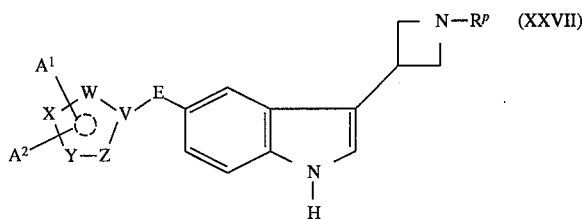

(XXVII)

wherein V, W, X, Y, Z, A¹, A², E and R$^p$ are as defined above; using methods analogous to those described above with reference to the compounds of formulae XII and XIII. Thus, for example, since Q in the compounds of formula XIII represents a reactive carboxylate moiety, the 1,2,4-triazole derivatives of formula XXVII may be prepared therefrom by reaction with a compound of formula A²—C(=NNHA¹)NH$_2$ or A²—C(=NNH$_2$)NHA¹.

In a yet further process, the compounds according to the invention wherein the group F is a benzofuran or benzthiophene moiety may be prepared by a method which comprises cyclising a compound of formula XXVIII:

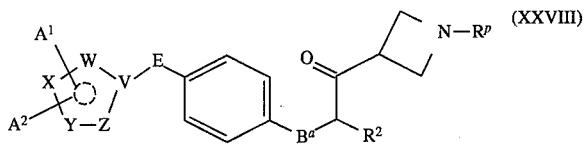

(XXVIII)

wherein V, W, X, Y, Z, A¹, A², E, R² amd R$^p$ are as defined above, and B$^a$ represents oxygen or sulphur; followed by removal of the protecting group R$^p$; and subsequently, where required, N-alkylation by standard methods to introduce the moiety R¹.

The cyclisation is conveniently effected by using polyphosphoric acid or a polyphosphate ester, advantageously at an elevated temperature.

The compounds of formula XXVIII may be prepared by reacting a compound of formula XXIX with a compound of formula XXX:

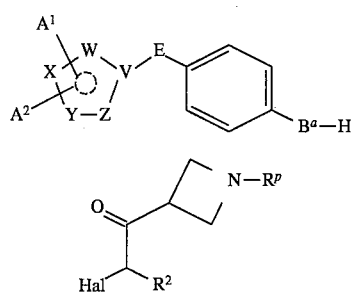

wherein V, W, X, Y, Z, A¹, A², E, B$^a$, R² and R$^p$ are as defined above, and Hal represents halogen.

The reaction is conveniently effected in the presence of a base such as sodium hydroxide.

The hydroxy and mercapto derivatives of formula XXIX may be prepared by a variety of methods which will be readily apparent to those skilled in the art. In one such method, the anion of a compound of formula XX as defined above is reacted with a compound of formula XXXI:

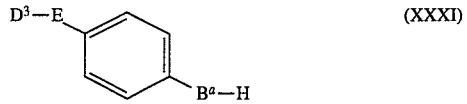

(XXXI)

wherein D³, E and B$^a$ are as defined above; to afford an intermediate of formula XXIX wherein V is nitrogen.

The compounds of formula XXX and XXXI, where they are not commercially available, may be prepared by standard procedures well known in the art.

The preparation of a typical intermediate of formula VII is illustrated by the following reaction scheme:

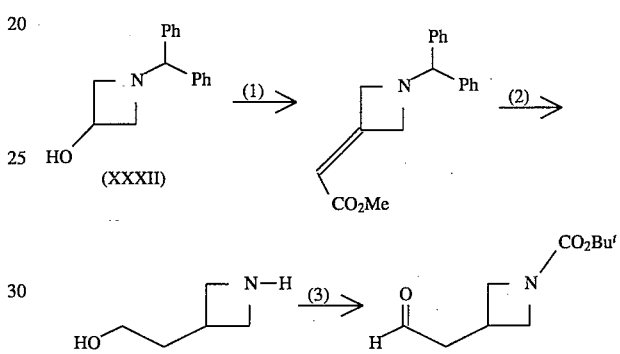

The starting compound XXXII is known from *J. Chem. Soc., Chem Commun.*, 1968, 93. Step 1 of the reaction scheme comprises oxidation of the hydroxy group of compound XXXII to a carbonyl group using pyridine.SO$_3$ in dimethyl sulphoxide (DMSO) and triethylamine; followed by reaction of the resulting azetidinone derivative with the Horner-Emmons reagent MeO$_2$C.CH$_2$.PO(OEt)$_2$ in the presence of sodium hydride, using tetrahydrofuran (THF) as the solvent. In Step 2, the double bond of the azetidine olefin ester is hydrogenated over palladium-charcoal in methanol; the methyl ester group is then reduced to hydroxymethyl by treatment with lithium aluminium hydride in THF; and the diphenylmethyl protecting group is in turn removed by treatment with palladium hydroxide on charcoal, with methanol serving as the solvent. Step 3 involves protection of the azetidine nitrogen as the N-t-butoxycarbonyl (N-BOC) carbamate derivative; and, finally, Swern oxidation of the side chain terminal hydroxy group to an aldehyde moiety by treatment with oxalyl chloride in DMSO/triethylamine.

It will be understood that any compound of formula I initially obtained from any of the above processes may, where appropriate, subsequently be elaborated into a further compound of formula I by techniques known from the art. Indeed, as will be appreciated, the compound of formula XV above in which R$^d$ is a group of formula —E—F is itself a compound of formula I in which A¹ is hydrogen and A² represents a non-bonded electron pair. In particular, a compound of formula I wherein R³ is hydrogen initially obtained may be converted into a compound of formula I wherein R³ represents C$_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Similarly, a compound of formula I wherein $R^1$ represents hydrogen initially obtained may be converted into a compound of formula I wherein $R^1$ is other than hydrogen, for example by conventional N-alkylation techniques, e.g. by treatment with the appropriate aldehyde in the presence of a reducing agent such as sodium cyanoborohydride, Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J.F.W. McOmie, Plenum Press, 1973; and T. W. Greene & P.G.M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

The ability of test compounds to bind to 5—$HT_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 riM) and mesulergine (100 nM) were included in the assay to block out 5—$HT_{1A}$ and 5—$HT_{1C}$ binding sites respectively. The concentration of the compounds of the accompanying Examples required to displace 50% of the specific binding ($IC_{50}$) is below 1 μM in each case.

The activity of test compounds as agonists of the 5—$HT_1$-like receptor was measured in terms of their ability to mediate contraction of the saphenous vein of New Zealand White rabbits, using the procedure described in *Arch. Pharm.*, 1990, 342, 111. Agonist potencies were calculated as $-log_{10}EC_{50}$ ($pEC_{50}$) values, from plots of percentage 5—HT (1 μm) response against the concentration of the agonist. The compounds of the accompanying Examples were found to possess $pEC_{50}$ values in this assay of not less than 5.0 in each case.

EXAMPLE 1

N-Methyl-3-[5-(2-methylimidazol-1-ylmethyl)-1H-indol-3yl] azetidine. Bisoxalate

INTERMEDIATE 1

N-tert-Butyloxycarbonyl-3-formylmethylazetidine

1. N-Diphenylmethylazetidin-3-ol

Aminodiphenylmethane (100 g, 0.54 mols) was added to a solution of epichlorohydrin (50 g, 0.54 mols) in DMSO (135 ml) and stirred at 25° C. for 3 days. The solution was then heated at 70° C. for 3 days before cooling to room temperature, adding 10% NaOH solution, and extracting with $Et_2O$ (2×800 ml). The combined extracts were washed with water (2×1), dried ($Na_2SO_4$) and evaporated. The crude product was chromatographed on silica-gel eluting with $CH_2Cl_2$/MeOH (98:2) to give the title-azetidinol (33.5 g); δ (360 MHz, $CDCl_3$) 2.30 (1H, br s, OH), 2.87–2.91 (2H, m, 2 of CH of $CH_2$), 3.51–3.55 (2H, m, 2 of CH of $CH_2$), 4.34 (1H, s, CH), 4.41–4.48 (1H, m, CH—OH), 7.13–7.39 (10H, m, Ar—H).

2. N-Diphenylmethylazetidin-3-one

Triethylamine (112.1 g, 1.11 mols) was added to a solution of N-diphenylmethylazetidin-3-ol (26.6 g, 0.11 mol) in DMSO (300 ml). The solution was cooled to 10° C. and a solution of sulphur trioxide-pyridine complex (112 g, 0.7 mol) in DMSO (500 ml) added, rapidly. Stirring was continued at 10° C. for 0.75h and the mixture then warmed to 25° C. and stirred for 1h. The solution was poured into ice-water (21) and extracted with EtOAc (3×1). The combined extracts were washed with water (500 ml) and brine (500 ml) and dried ($Na_2SO_4$). The crude product was purified by chromatography through silica-gel eluting with petroleum ether/EtOAc (2:1) to give the desired ketone (25.8 g), mp 74°–75° C.; δ (360 MHz, $CDCl_3$) 4.00 (4H, s, 2 of $CH_2$), 4.59 (1H, s, CH), 7.19–7.49 (10H, m, Ar—H).

3. Methyl (1-diphenylmethylazetidin-3-ylidene)acetate

Methyl diethylphosphonoacetate (1 1.0 g, 52.0 retool) in THF (10 ml) was added dropwise to a stirred suspension of sodium hydride (2.1 g, 60% dispersion in oil, 52.5 mmol) in THF (40 ml), at 10° C. The mixture was stirred for 0.6 h and a solution of the preceding azetidinone (11.3 g, 48.0 mmol) in THF (50 ml) then added dropwise at 10° C. The mixture was heated at 50° C. for 3 h before removing the solvent under vacuum and redissolving the residue in $CH_2Cl_2$ (200ml). The solution was washed with water (50 ml) and sodium bisulphite solution (2×50 ml) and dried ($Na_2SO_4$). Chromatography of the residue obtained, after removing the solvent, through silica-gel eluting with $CH_2Cl_2$/MeOH (98:2) gave the desired ester (13.1 g), mp 83°–84° C.; δ (360 MHz, $CDCl_3$) 3.65 (3H, s, $CO_2Me$), 3.88 (2H, m, 2 of CH of $CH_2$), 4.14–4.17 (2H, m, 2 of CH of $CH_2$), 4.52 (1H, s, CH), 5.65–5.68 (1H, m, vinyl-H), 7.17–7.44 (10H, m, Ar—H).

4. N-Diphenylmethyl-3-carbomethoxymethylazetidine

A mixture of the compound from step 3 (21.0 g, 71.7 mmol), $Pd(OH)_2$ (3.0 g, 20% on C), methanol (500 ml) and 2N HCl (37 ml) was hydrogenated on a Parr shake apparatus for 2 h. The catalyst was removed by filtration through celite and the solvents removed under vacuum. Saturated $K_2CO_3$ solution was added (50ml) and extracted with $CH_2Cl_2$ (2×250 ml). The combined extracts were washed with $H_2O$ (250 ml) and brine (100 ml), dried ($Na_2SO_4$) and evaporated to give the title-product as a pale yellow oil (19.3 g); δ (360 MHz, $CDCl_3$) 2.58 (2H, d, J=7.3 Hz, $CH_2$), 2.75–2.81 (3H, m, 2 of CH of $CH_2$ and CH), 3.35–3.38 (2H, m, 2 of CH of $CH_2$), 3.62 (3H, s, $CO_2Me$), 4.31 (1H, s, CH), 7.14–7.18, 7.23–7.27 and 7.38–7.40 (total 10H, each m, Ar—H).

5. Ethyl-2-(1-diphenylmethylazetidin-3-yl)alcohol

Diisobutylaluminium hydride (119 ml of a 1M solution in toluene, 0.119 mol) was added dropwise to a stirred solution of the preceding ester (10.0 g, 33.9 mmol) in toluene (500 ml), at −35° C., over a 0.5h period. The solution was warmed to 25° C., stirred for 2h, and then cooled to 0° C. and quenched by addition of methanol (10 ml), 2N NaOH (5 ml) and H$_2$O (5 ml). The mixture was warmed to 25° C., filtered through celite and the solvent removed under vacuum. The residue was chromatographed on silica-gel eluting with ethyl acetate/hexane (1:1) to give the title-alcohol as a white crystalline solid, (4.1 g), mp 98°–99° C.; (Found: C, 80.73; H, 8.06; N, 5.38. C$_{18}$H$_{21}$NO requires C, 80.86; H, 7.92; N, 5.24%); δ (360 MHz, CDCl$_3$) 1.64 (1H, br s, OH), 1.82 (2H, m, CH$_2$), 2.51–2.58 (1H, m, CH), 2.87–2.91 and 3.29–3.33 (both 2H, each m, 2 of CH$_2$), 3.70 (2H, t, J=6.4 Hz, CH$_2$), 4.33 (1H, s, CH), 7.15–7.40 (10H, m, Ar—H).

6. Ethyl-2-( 1-H-azetidin-3-yl)alcohol. Hydrochloride

Pd(OH)$_2$ (0.8 g, 20% on C) was added to a solution of the preceding alcohol (4.0 g, 15.0 retool) in methanol (200 ml) and 1N HCl (10 ml), and the mixture hydrogenated on a Parr shake apparatus for 24h, at 55 psi. The mixture was filtered through celite and the solvent removed under vacuum. Diphenyl methane was removed by triturating the residue with ether and decanting. The remaining product was dried under vacuum to give the desired product (2.0 g); δ (250 MHz, D$_2$O) 1.86–1.94 (2H, m, CH$_2$), 2.98–3.16 (1H, m, CH), 3.60 (2H, t, J=6.4 Hz, CH$_2$), 3.86–3.96 and 4.14–4.22 (both 2H, both m, 2 of CH$_2$).

7. Ethyl-2-( 1-tert-butyloxycarbonylazetidin-3-yl)alcohol

A mixture of the product from step 6 (1.44 g, 10.5 mmol), triethylamine (3.21 ml, 22.9 mmol) and (BOC)$_{2}$O (3.43 g, 15.7 mmol), in THF (90 ml) was stirred at 25° C. for 2 days. The solvent was removed under vacuum, water (70 ml) added and extracted with EtOAc (3 x). The combined extracts were dried (MgSO$_4$), evaporated and the residue chromatographed on silica-gel eluting with CH$_2$Cl$_2$/MeOH (95:5) to give the title-product (2.12 g); δ (250 MHz, CDCl$_3$) 1.42 (9H, s, 3 of CH$_3$), 1.56 (1H, s, OH), 1.82–1.90 (2H, m, CH$_2$), 2.56–2.76 (1H, m, CH), 3.58–3.67 (4H, m, CH$_2$ and 2 of CH of CH$_2$), 4.00–4.06 (2H, m, 2 of CH of CH$_2$).

8. N-tert-Butyloxycarbonyl-3-formylmethylazetidine

Dimethylsulphoxide (1.98 g, 25.3 mmol) was added dropwise to a solution of oxalyl chloride (1.61 g, 12.6 mmol) in CH$_2$Cl$_2$ (80 ml), at −75° C. The mixture was stirred for 0.25h before adding a solution of the preceding alcohol (2.12 g, 10.6 mmol) in CH$_2$Cl$_2$ (50 ml), at −75° C., and stirring for 1h. Triethylamine (5.38 g, 52.7 mmol) was added and the reaction mixture warmed to 25° C. and stirred for 1h. Water (50 ml) and saturated K$_2$CO$_3$ solution (25 ml) were added and the mixture stirred vigorously before separation of the aqueous phase and further extraction with CH$_2$Cl$_2$ (2 x). The combined extracts were dried (MgSO$_4$), the solvent removed under vacuum, and the crude product chromatographed on silica-gel eluting with diethyl ether. The desired product (1.9g) was obtained as a pale yellow solid, mp 52°–54° C.; (Found: C, 60.05; H, 8.57; N, 7.09. C$_{10}$H$_{17}$NO$_3$ requires C, 60.28; H, 8.6; N, 7.03%); δ (360 MHz, CDCl$_3$) 1.34 (9H, s, 3 of CH$_3$), 2.76 (2H, d, J=7.4 Hz, CH$_2$CHO), 2.77–2.96 (1H, s, CH), 3.46–3.52 (2H, m, 2 of CH of CH$_2$), 4.02–4.08 (2H, m, of CH of CH$_2$), 9.70 (1H, s, aldehyde-H).

INTERMEDIATE 2

4-(2-Methylimidazol-1-ylmethyl)phenylhydrazine Hydrochloride 1. 4-(2-Methylimidazol-1-ylmethyl)nitrobenzene Sodium hydride (2.45 g, 61.0 mmol, 60% dispersion in oil) was added to a solution of 2-methylimidazole (5.0 g, 60.9 mmol) in DMF (100 ml). The mixture was stirred at room temperature for 0.25h before adding 4-nitrobenzyl bromide (13.2 g, 61.0 mmol) and heating at 110° C. for 2h followed by stirring at room temperture for 16h. Water (200 ml) and ethyl acetate (500 ml) were added, the aqueous separated and extracted with ethyl acetate (2×500 ml). The combined extracts were washed with water (3×250 ml), dried (MgSO$_4$) and evaporated. The crude product was chromatographed on silica-gel eluting with CH$_2$Cl$_2$/MeOH (96:4) to give the title-product (1.58 g); δ (360 MHz, CDCl$_3$) 2.34 (3H, s, CH$_3$), 5.16 (2H, s, CH$_2$), 6.67 (1H, d, J=1.3 Hz, Ar—H), 7.03 (1H, d, J=1.3 Hz, Ar—H), 7.19 (2H, d, J=9.5Hz, Ar—H), 8.22 (2H, d, J=9.5Hz, Ar—H).

2. 4-(2-Methylimidazol-1-ylmethyl)phenylaniline Hydrochloride

Pd-C (1.5 g, 10%) was added to a mixture of the preceding nitrobenzene (14.4 g, 66.4 mmol), water (12 ml), 5N HCl (14.6 ml), and ethanol (85 ml) and the slurry hydrogenated at 40 psi in a Parr flask for 0.5h. The catalyst was removed by filtration through celite, the solvents removed under vacuum, and the resulting solid recrystallised from EtOH/Et$_2$O to give the title-aniline (12.0 g); a (360 MHz, D$_2$O) 2.62 (3H, s, CH$_3$), 5.21 (2H, s, CH$_2$), 6.90 (2H, d, J=8.4 Hz, Ar—H), 7.19 (2H, d, J=8.4 Hz, Ar—H), 7.31 (2H, s, Ar—H).

3. 4-(2-Methylimidazol-1-ylmethyl)phenylhydrazine Hydrochloride

A solution of NaNO$_2$ (5.21 g, 76.5 mmol) in H$_2$O (70 ml) was added to a stirred solution of the preceding aniline hydrochloride (15.34 g, 68.6 mmol) in concn. HCl (140 ml), cooled to −15° C. After addition (0.25h) the mixture was stirred for 0.5h at −15° C. and then filtered through a sinter directly into an addition funnel. The resulting solution was added to a rapidly stirred solution of SnCl$_2$.2H$_2$O (61.9 g, 0.275 mol) in conc$^n$.HCl (100 ml) at such a rate as to maintain the temperature below −5° C. The mixture was warmed to room temperature, the precipitate filtered off, and the solid washed several times with Et$_2$O. In order to remove tin salts the free base was generated by dissolving in H$_2$O (120 ml), basifying with NH$_4$OH solution and extracting with CH$_2$Cl$_2$ (2 x). The hydrochloride salt was regenerated by addition of ethereal HCl to the CH$_2$Cl$_2$ solution of the free base. The product was filtered and dried under vacuum (11.4 g); δ (360 MHz, D$_2$O) 2.62 (3H, s, CH$_3$), 5.26 (2H, s, CH$_2$), 7.02 (2H, d, J=8.4 Hz, Ar—H), 7.28 (2H, d, J=8.4 Hz, Ar—H), 7.29 (1H, d, J=1.5 Hz, Ar—H), 7.30 (1H, d, J=1.5 Hz, Ar—H).

N-Methyl-3-[5-(2-methylimidazol-1-ylmethyl)-1H-indol-3-yl] azetidine. Bisoxalate

1.

1H-3-[5-(2-Methylimidazol-1-ylmethyl)-1H-indol-3-yl] azetidine

N-tert-Butyloxycarbonyl-3-formylmethylazetidine (0.3 g, 1.51 mmol) was added to a solution of 4-(2-methylimidazol-1-ylmethyl)phenylhydrazine (0.36 g, 1.51 mmol) in 4% H$_2$SO$_4$ (25 ml) and the resulting solution refluxed for 3h. The mixture was then cooled to room temperature, basified with K$_2$CO$_3$ and extracted with n-butanol (2×100 ml). The combined extracts were dried (MgSO$_4$), evaporated, and the residue chromatographed through silica-gel eluting with CH$_2$Cl$_2$/MeOH/NH$_3$ (20:8:1) to give the title-indole (0.186 g, 46%), mp 88°–90° C.; δ (250 MHz, CD$_3$OD) 2.02 (3H, s, CH$_3$), 3.76–3.86 (4H, m, 2 of CH$_2$), 4.04–4.20 (1H, m, CH of azetidine), 5.06 (2H, s, CH$_2$), 6.70 (1H, d, J=1.4 Hz, Ar—H), 6.82 (1H, dd, J=1.5 and 8.4 Hz, Ar—H), 6.90 (1H, d, J=1.4 Hz, Ar—H), 7.12 (1H, s, Ar—H), 7.23 (1H, d, J = 8.4Hz, At-H), 7.26 (1H, d, J = 1.5Hz, Ar—H).

2.
N-Methyl-3-[5-(2-methylimidazol-1-ylmethyl)-1H-indol-3-yl] azetidine. Bisoxalate To a cooled and stirred solution of the preceding 1H-azetidine (0.174 g, 0.65 mmol), NaCNBH$_3$ (5 mg, 0.82 mmol), and acetic acid (98 mg, 1.64 mmol), in methanol (20 ml), was added a solution of formaldehyde (65 mg, 0.82 mmol; 38% w/v) in methanol (10 ml), at such a rate as to keep the temperature of the solution at 0° C. The mixture was stirred at 0° C. for 0.25h and then warmed to room temperature and stirred for 1h. Saturated K$_2$CO$_3$ solution (15 ml) was added and the methanol removed under vacuum. The aqueous was extracted with EtOAc (3×100 ml), the combined extracts dried (MgSO$_4$) and the solvent removed under vacuum. The residue was chromatographed on silica-gel eluting with CH$_2$Cl$_2$/MeOH/NH$_3$ (70:8:1) and the bisoxalate salt of the resulting product was prepared (91 mg), mp 125°–126° C.; (Found: C, 53.03; H, 5.27; N, 11.17. C$_{17}$H$_{20}$N$_4$.2.2(C$_2$H$_2$O$_4$).0.30H$_2$O.0.1(CH$_3$OH) requires C, 53.02; H, 5.26; N, 11.50%); m/e 281 (M$^+$+1); δ (360 MHz, D$_2$O) 2.64 (3H, s, CH$_3$), 3.00 and 3.09 (total 3H, both s, N-CH$_3$), 4.17–4.24, 4.38–4.58 and 4.74–4.86 (total 5H, both m, CH and 2 of CH$_2$ of azetidine), 5.41 (2H, s, CH$_2$), 7.18–7.20 (1H, m, Ar—H), 7.31 (2H, s, Ar—H), 7.53 (1H, d, J=1.0 Hz, Ar—H), 7.56–7.59 (2H, m, Ar—H).

EXAMPLE 2

N-Methyl-3-[5-(1,2,4-triazol-1-yl)-1H-indol-3-yl]azetidine. Oxalate

1. 4-(1,2,4-Triazol-1-yl)nitrobenzene 1,2,4-Triazole sodium derivative (90%) (17.74 g, 0.18 mol) and 1-fluoro-4-nitrobenzene (25 g, 0.18 mol), in DMF, (150 ml) was stirred at room temperature for 4 days. Water (300 ml) and ethyl acetate (500 ml) were added and the mixture extracted. The organic layer was separated, washed with water (3×300 ml), dried (MgSO$_4$) and evaporated to give the desired product (24.8 g); δ (360 MHz, CDCl$_3$) 7.92 (2H, d, J=9.1 Hz, Ar—H), 8.17 (1H, s, Ar—H), 8.40 (2H, d, J=9.1 Hz, Ar—H), 8.48 (1H, s, Ar—H).

2. 4-(1,2,4-Triazol-1-yl)phenylhydrazine

Prepared from 4-(1,2,4-triazol-1-yl)nitrobenzene using the procedure described for the preparation of Intermediate 2; δ (360 MHz, CDCl$_3$) 3.66 (2H, br s, NH$_2$), 5.36 (1H, br s, NH), 6.88–6.96 and 7.44–7.50 (both 2H, both m, Ar—H), 8.06 (1H, s, ArH), 8.42 (1H, s, Ar—H).

3. 1H-3-[5-(1,2,4-triazol-1-yl)-1H-indol-3-yl]azetidine

N-tert-Butyloxycarbonyl-3-formylmethylazetidine (0.4 g, 2.01 mmol) was added to a solution of 4-(1,2,4-triazol-1-yl)phenylhydrazine (0.35 g, 2.01 mmol) in 4% H$_2$SO$_4$ (50 ml) and the mixture refluxed for 16h. The mixture was then cooled to room temperature, basified (K$_2$CO$_3$) and extracted with n-butanol (5 x). The crude product obtained was chromatographed on silica-gel eluting with CH$_2$Cl$_2$/MeOH/NH$_3$ (20:8:1) to give the title-azetidinylindole (0.186 g, 39%); δ (360 MHz, CD$_3$OD) 3.80–3.88 (4H, m, 2 of CH$_2$ of azetidine), 4.12–4.23 (1H, m, CH), 7.23 (1H, s, Ar—H), 7.39 (2H, s, Ar—H), 7.65 (1H, d, J=2.5 Hz, Ar—H), 8.04 (1H, s, Ar—H), 8.89 (1H, s, Ar—H).

4. N-Methyl-3-[5-(1,2,4-triazol-1-yl)-1H-indol-3-yl]azetidine. Oxalate

Prepared from the product of step 3 using the procedure described for Example 1. The oxalate salt was prepared, mp 175°–177° C.; (Found: C, 54.17; H, 5.15; N, 19.04. C$_{14}$H$_{15}$N$_5$.1.2(C$_2$H$_2$O$_4$).0.125H$_2$O requires C, 54.17; H, 4.89, N, 19.26%); δ (360 MHz, D$_2$O) 2.99 and 3.07 (total 3H, s, CH$_3$), 4.17–4.22, 4.35–4.57 and 4.72–4.79 (total 5H, m, azetidine-H), 7.42–7.47 (1H, m, Ar—H), 7.53 (1H, s, Ar—H), 7.58–7.62 (1H, m, ArH), 7.74–7.76 (1H, m, Ar—H), 8.22 (1H, s, Ar—H), 9.82 (1H, s, Ar—H).

EXAMPLE 3

N-Methyl-3-[5-imidazol-1-yl-1H-indol-3-yl]azetidine. Hemioxalate. Monohydrate

1. 4-Imidazol-1-ylphenylhydrazine. Dihydrochloride

Prepared from imidazole and 1-fluoro-4-nitrobenzene as described for Example 2, step 1 and Intermediate 2; δ (360 MHz, D$_2$O) 7.36–7.46 (2H, m, Ar—H), 7.80–7.88 (3H, m, Ar—H), 8.04–8.06 (1H, m, Ar—H), 9.30 (1H, s, Ar—H).

2. 1H-3-[5-Imidazol-1-yl-1H-indol-3-yl]azetidine

The title-compound was prepared from 4-imidazol-1-ylphenylhydrazine dihydrochloride using the procedure described for Example 2, step 3; δ (360 MHz, CD$_3$OD) 4.05–4.16 and 4.26–4.34 (total 5H, each m, azetidine-H), 7.04 (1H, s, Ar—H), 7.20 (1H, dd, J=2.0 and 8.6Hz, Ar—H), 7.33 (1H, s, Ar—H), 7.42 (1H, d, J=8.6 Hz, Ar—H), 7.43 (1H, s, Ar—H), 7.64 (1H, d, J=2.0 Hz, Ar—H), 7.95 (1H, s, Ar—H).

3. N-Methyl-3-[5-imidazol-1-yl-1H-indol-3-yl]azetidine. Hemioxalate. Monohydrate Prepared from the preceding 1H-azetidine using the procedure described for Example 1. The hemioxalate monhydrate salt was prepared, mp 215°– 218° C.; (Found: C, 61.24; H, 6.14; N, 17.01. C$_{15}$H$_{16}$N$_4$.0.5(C$_2$H$_2$O$_4$).0.9H$_2$O requires C, 61.29; H, 6.04; N, 17.87%); m/e 253 (M$^+$+1); δ (360 MHz, D$_2$O) 3.04 and 3.12 (total 3H, each s, CH$_3$), 4.22–4.27, 4.43–4.62 and 4.78–4.86 (total 5H, each m, azetidine-H), 7.39 (1H, s, Ar—H), 7.40 (1H, d, J=8.6Hz, Ar—H), 7.61 (1H, s, Ar—H), 7.65–7.71 (3H, m, At-H), 8.45 (1H, s, Ar—H).

EXAMPLE 4

N-Methyl-3[5-(1-methyl tetrazol-5-ylmethyl)-1H-indol-3-yl] azetidine. Succinate. Monohydrate

1. 4-(1H-Tetrazol-5-ylmethyl)nitrobenzene

Triethylamine hydrochloride (41.25 g, 0.3 mol) and sodium azide (39 g, 0.6 mol) were added to a solution of 4-nitrophenylacetonitrile (32.4 g, 0.2 mmol) in anhydrous N-methylpyrrolidin- 2-one (500 ml) and the mixture heated at 150° C. for 4h. The solution was cooled to room temperature and poured into 2N HCl (2 1) whereupon a solid crystallised out. The product was filtered, washed with water (500 ml) and hexane and dried in vacuo (37.4 g); δ (250 MHz, CDCl$_3$) 4.34 (2H, s, CH$_2$), 7.42 (2H, d, J=8.7 Hz, Ar—H), 8.12 (2H, d, J=8.7 Hz, Ar—H).

2. 4-(1-Methyltetrazol-5-ylmethyl)nitrobenzene

A solution of methyl iodide (34.1 ml, 0.5 mol) in acetonitrile (100 ml) was added dropwise, over 1h, to a solution of 4-(1H-tetrazol-5-ylmethyl)nitrobenzene (20.5 g, 0.1 mmol), and triethylamine (18.7 ml, 0.25 mol), in acetonitrile (500 ml), at room temperature. The mixture was stirred for 3h, the solvent removed under vacuum and residue dissolved in EtOAc (500 ml). The solution was washed with water (2x) and brine (1x) and the solvent evaporated. The crude product was chromatographed through silica-gel eluting with EtOAc/hexane (1:1)→EtOAc (100%) to give 2 components. The more polar product (7.9 g) was identified as the desired 1-methyl substituted tetrazole. The less polar product (7.0 g) was identified as being the 2-substitution product; δ (360 MHz, CDCl$_3$, more polar isomer) 3.94 (3H, s, CH$_3$), 4.40 (2H, s, CH$_2$), 7.42 (2H, d, J= 8.7 Hz, Ar—H), 8.21 (2H, d, J=8.7Hz, Ar—H).

3. 4-(1-Methyltetrazol-5-ylmethyl)phenylhydrazine. Hydrochloride

The title-hydrazine was prepared from the preceding nitrobenzene using the procedures described for Intermediate 2; δ (360 MHz, D$_2$O) 4.02 (3H, s, CH$_3$), 4.32 (2H, s, CH$_2$), 7.05 (2H, d, J=8.5 Hz, Ar—H), 7.31 (2H, d, J=8.5 Hz, Ar—H).

4. 1H-3-[5-(1-Methyltetrazol-5-ylmethyl)-1H-indol-3yl] azetidine

The title-compound was prepared from the preceding hydrazine and N-tert-butyloxycarbonyl-3-formylmethyl azetidine according to the procedure described for Example 1, mp 85°–87° C.; (Found: C, 62.89; H, 6.25; N, 30.14. C$_{14}$H$_{16}$N$_6$.0.15(C$_2$H$_2$OH) requires C, 62.40; H, 6.19; N, 30.53%); δ (360 MHz, CD$_3$OD) 3.68–3.90 (4H, m, 2 of CH$_2$), 3.80 (3H, s, CH$_3$), 4.03–4.20 (1H, m, CH of azetidine), 4.32 (2H, s, CH$_2$), 6.85 (1H, dd, J=1.5 and 8.4 Hz, Ar—H), 7.12 (1H, s, Ar—H), 7.22 (1H, d, J=8.4 Hz, Ar—H), 7.38 (1H, d, J=1.5 Hz, Ar—H).

5. N-Methyl,3-[5-(1-methyltetrazol-5-ylmethyl)-1H-indol-3yl] azetidine. Succinate. Monohydrate Prepared from the preceding 1H-azetidine using the general N-methylation procedure. The succinate monohydrate salt was prepared, mp 65°–67° C.; (Found: C, 57.25; H, 6.59; N, 22.17. C$_{15}$H$_{18}$N$_6$.0.7(C$_4$H$_6$O$_4$).0.5H$_2$O requires C, 57.16; H, 6.25; N, 22.45%); δ (360 MHz, D$_2$O) 2.41 (2H, s, succinic acid), 2.97 and 3.06 (total 3H, both s, CH$_3$), 3.97 (3H, s, CH$_3$), 4.13–4.19, 4.27–4.51 and 4.69–4.74 (total 5H, each m, azetidine H), 4.40 (2H, s, CH$_2$), 7.11 (1H,.d, J=8.4 Hz, Ar—H), 7.44 (2H, s, Ar—H), 7.49 (1H, d, J=8.4Hz, Ar—H).

EXAMPLE 5

N-Methyl-3-[5-(2-(1-methyltetrazol-5-yl)ethyl)-1H-indol-3yl] azetidine. Benzoate The title-compound was prepared from 4-nitrophenethyl nitrile as described for Example 4. The benzoate salt was prepared, mp 165°–167° C.; (Found: C, 66.30; H, 6.33; N, 20.15.C$_{16}$H$_{20}$N$_6$.C$_7$H$_6$O$_2$ requires C, 66.01; H, 6.26; N, 20.08%); δ (250 MHz, D$_2$O) 3.04 and 3.14 (total 3H, both s, CH$_3$), 3.20–3.38 (4H, m, 2 of CH$_2$), 3.56 and 3.60 (total 3H, both s, CH$_3$), 4.12–4.20, 4.28–4.54 and 4.68–4.84 (total 5H, each m, azetidine-H), 7.08–7.18, 7.43–7.64 and 7.90–7.96 (total 9H, m, Ar—H and benzoic acid).

EXAMPLE 6

N-Methyl -3-[5-(1,2,4-triazol-1-ylmethyl)-1H-indol-3-yl] azetidine. Hemioxalate

Prepared from N-tert-butyloxycarbonyl-3-formylazetidine and 4-(1,2,4-triazol-1-ylmethyl)nitrobenzene using the procedures described for Example 1. The hemioxalate salt was prepared, mp 100°–102° C.; (Found: C, 60.26; H, 6.09; N, 20.03. C$_{15}$H$_{17}$N$_5$.0.65(C$_2$H$_2$O$_4$).0.2 (Et$_2$O).0.1H$_2$O requires C, 59.97; H, 6.03; N, 20.45%); δ (360 MHz, D$_2$O) 3.00 and 3.09 (total 3H, both s, N—CH$_3$), 4.16–4.22, 4.33–4.56 and 4.71–4.77 (total 5H, each m, CH and 2 of CH$_2$ of azetidine), 5.50 (2H, s, CH$_2$), 7.22–7.24, 7.47–7.56 and 7.90–7.92 (total 4H, each m, Ar—H), 8.05 and 8.54 (total 2H, each s, Ar—H).

EXAMPLE 7

N-Methyl-3-[5-(1,2,4-triazol-4-yl)-1H-indol-3-yl]azetidine. 1.75 Benzoate. 0.8 Hydrate 1. 4-(1,2,4-Triazol-4-yl)phenylhydrazine a) 4'-Aminoacetanilide A solution of 4'-nitroacetanilide (5.0 g, 27.8 mmol) in EtOH/EtOAc (160 ml, 1:1), H$_2$O (15 ml) and 5N HCl (5.6 ml, 28.0 mmol) was hydrogenated over 10% Pd-C (0.50 g) at 50 psi for 0.25h. The catalyst was removed by filtration through celite and the solvents removed under vacuum. The free base was generated by dissolving the product in H$_2$O basifying with 2N NaOH and extracting into EtOAc. The combined extracts were dried (MgSO$_4$) and evaporated to give the title-aniline (3.75 g, 90%); δ (250 MHz, CDCl$_3$/D$_4$—MeOH) 2.10 (3H, s, CH$_3$), 6.68 (2H, d, J=8.8 Hz, Ar—H), 7.27 (2H, d, J=8.8 Hz, Ar—H).

b) 4'-(1,2,4-Triazo-4-yl)acetanilide

A mixture of the preceding aniline (3.52 g, 23.4 mmol), N,N-dimethylformamide azine (3.33 g, 23.4 mmol; *J. Chem. Soc. C.* 1967, 1664) and p-toluenesulphonic acid monohydrate (0.223 g, 1.17 mmol), in anhydrous toluene (100 ml), was heated at reflux for 17h. The beige coloured precipitate was filtered off and washed with toluene and CH$_2$Cl$_2$ and dried under vacuum to give the desired triazole (4.29 g, 91%); δ (250 MHz, D$_4$—MeOH, D$_6$—DMSO) 2.14 (3H, s, CH$_3$), 7.60 (2H, d, J=8.8 Hz, Ar—H), 7.78 (2H, d, J=8.8Hz, Ar—H), 8.96 (2H, s, Ar—H).

c) 4'-(1,2,4-Triazol-4-yl)phenylaniline

A solution of the preceding acetanilide (4.91 g, 24.3 mmol) in 5N HCl (100 ml) was heated at 125° C. for 1.5h. The mixture was cooled to 0° C., basified with conc. aqueous NaOH solution and extracted with CH$_2$Cl$_2$ (×5). The combined extracts were dried (MgSO$_4$) and evaporated and the residue chromatographed on silica-gel eluting with CH$_2$Cl$_2$/MeOH/NH$_3$ (80:8:1) to give the title-aniline (2.94 g, 76%); δ (250 MHz, CDCl$_3$) 3.80 (2H, s, NH$_2$), 6.71 (2H, d, J=8.8 Hz, Ar—H), 7.08 (2H, d, J = 8.8 Hz, Ar—H), 8.36 (2H, s, Ar—H).

d) 4'-(1,2,4-Triazol-4-yl)phenylhydrazine

Prepared from the preceding aniline using the procedure described for Example 1, Intermediate 2; δ (250 MHz, CDCl$_3$) 3.51 (3H, br s, NHNH$_2$), 6.96 (2H, d, J=8.8Hz, Ar—H), 7.23 (2H, d, J=8.8 Hz, Ar—H), 8.44 (2H, s, Ar—H).

N-Methyl-3-[5-(1,2,4-triazol-4-yl)-1H-indol-3-yl]azetidine. 1.75 Benzoate. 0.8 Hydrate Prepared from the preceding hydrazine and N-tert-butyloxycarbonyl- 3-formylazetidine using the procedures described for Examples 1 and 2. The 1.75 benzoate 0.8 hydrate salt was prepared, mp ≈30° C. (hygroscopic); (Found: C, 65.66; H, 5.97; N, 14.53. C$_{14}$H$_{15}$N$_5$.1.75 C$_6$H$_5$CO$_2$H.0.8H$_2$O requires C, 65.49; H, 5.67; N, 14.55%); m/e 254 (M+1)$^+$; δ (360 MHz, D$_2$O) 2.98 and 3.07 (total 3H, each s, N-CH$_3$), 4.16–4.22, 4.35–4.56 and 4.72–4.77 (total 5H, each m, CH and 2 of CH$_2$ of azetidine), 7.28–7.34, 7.43–7.64 and 7.88–7.90 (total 12H, each m, Ar—H and benzoic acid), 8.78 (2H, s, Ar—H).

EXAMPLE 8

N-Methyl-3-[5-(imidazol-1-ylmethyl)-1H-indol-3-yl]azetidine. 1.5 Benzoate. 0.7 Hydrate Prepared from N-tert-butyloxycarbonyl-3-fomyl azetidine and 4-(imidazol-1-ylmethyl)nitrobenzene using the procedures described for Example 1. The 1.5 benzoate 0.7 hydrate salt was prepared, mp: ≈45° C. (hygroscopic); (Found: C, 69.07; H, 6.64; N, 11.97. C$_{16}$H$_{18}$N$_4$.1.5C$_6$H$_5$CO$_2$H.0.7H$_2$O requires C, 68.87; H, 6.19; N, 12.12%); m/e 267 (M+1)$^+$; δ (360MHz, D$_6$-DMSO) 2.39 (3H, s, N-CH$_3$), 3.28–3.82 (5H, m, CH and 2 of CH$_2$ of azetidine), 5.20 (2H, s, CH$_2$), 6.86 (1H, s, Ar—H), 7.01 (1H, dd, J=1.5 and 8.4Hz, Ar—H), 7.16 (1H, s, Ar—H), 7.29 (1H, s, Ar—H), 7.31 (1H, d, J=8.4 Hz, Ar—H), 7.45–7.60 (6H, m, Ar—H), 7.73 (1H, s, Ar—H), 7.92–7.95 (3H, m, Ar—H), 10.96 (1H, s, NH).

EXAMPLE 9

Tablet Preparation

Tablets containing 1.0, 2.0, 25.0, 26.0, 50.0 and 100.0 mg, respectively of the following compounds are prepared as illustrated below:

N-Methyl-3-[5-(2-methylimidazol-1-ylmethyl)-1H-indol-3-yl] azetidine. Bisoxalate N-Methyl-3-[5-(1,2,4- triazol-1-yl)-1H-indol-3-yl]azetidine. Oxalate N-Methyl-3-[5-imidazol-1-yl-1H-indol-3-yl]azetidine. Hemioxalate. Monohydrate N-Methyl-3-[5-(1-methyltetrazol-5-ylmethyl)-1H-indol-3-yl] azetidine. Succinate. Monohydrate N-Methyl-3-[ 5-(2-(1-methyltetrazol-5-yl)ethyl )-1H-indol-3-yl] azetidine. Benzoate N-Methyl-3-[5-(1,2,4-triazol-1-ylmethyl)-1H-indol-3-yl] azetidine. Hemioxalate N-Methyl-3-[5-(1,2,4-triazol-4-yl)-1H-indol-3-yl]azetidine. 1.75 Benzoate. 0.8 Hydrate N-Methyl-3-[5-(imidazol-1-ylmethyl)-1H-indol-3-yl] azetidine. 1.5 Benzoate. 0.7 Hydrate

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

We claim:
1. A compound of Fonnula I, or a pharmaceutically acceptable salt or prodrug thereof:

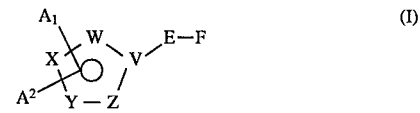

wherein the circle represents two non-adjacent double bonds in any position in the five-membered ring:

two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring;

A$^1$ represents hydrogen, hydrocarbon, a heterocyclic group, halogen, cyano, trifluoromethyl, —OR$^x$, —SR$^x$, —NR$^x$R$^y$, —NR$^x$CO$_2$R$^y$, —NR $^x$CO$_2$R$^y$, —NR $^x$SO$_2$R$^y$, or —NR$^z$CTNR$^x$R$^y$:

A$^2$ represents a non-bonded electron pair when four of V, W, X, Y and Z represent nitrogen and the other represents carbon; or, when two or three of V, W, X, Y and Z represent nitrogen and the remainder represent carbon, A$^2$ represents hydrogen, hydrocarbon. a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$ SO2R$^r$, or —NR$^z$CTNR$^x$R$^y$: wherein A$^1$ and A$^2$ can further be independently substituted by trifluoromethyl, C$_{1-6}$ alkoxy, C$_{2-6}$ alkoxycarbonyl, C$_{2-6}$ alkylcarbonyl, C$_{1-6}$ alkylsulphonyl, arylsulphonyl, amino, mono-or di(C$_{1-6}$)alkylamino, C$_{2-6}$ alkylcarbonylamino, arylcarbonylamino, (C$_{2-6}$ alkoxycarbonylamino, C$_{1-6}$ alkylsulphonylamino, arylsulphonylamino, C$_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminoxulphonylmethyl;

E represents a bond or a straight or branched alkylene chain containing 1 to 4 carbon atoms;

F represents a group of formula

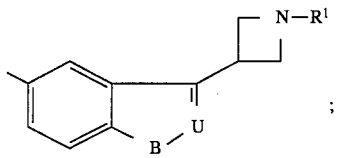

U represents nitrogen or C-$R^2$;

B represents oxygen, sulphur or N-$R^3$;

$R^1$, $R^2$ and $R^3$ independently represent hydrogen or $C_{1-6}$ alkyl;

$R^x$ and $R^y$ independently represent hydrogen, hydrocarbon or a heterocyclic group, or $R^x$ and $R^y$ together represent a $C_{2-6}$ alkylene group;

$R^z$ represents hydrogen, hydrocarbon or a heterocyclic group; represents oxygen, sulphur or a group of formula =$N_fG$; and G represents hydrocarbon. a heterocyclic group or a electron-withdrawing group.

2. A compound as claimed in claim 1 represented by formula IIA, or a pharmaceutically acceptable salt or prodrug thereof:

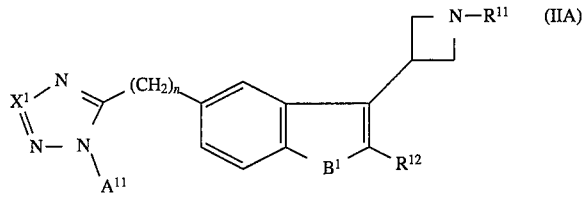

wherein $X^1$ represents nitrogen or $A^{12}$-C;

n is zero, 1, 2 or 3;

$B^1$ represents oxygen, sulphur or N-$R^{13}$;

$A^{11}$ and $A^{12}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted as defined in claim 1; or hydrogen, halogen, cyano, trifluoromethyl or amino; and $R^{11}$, $R^{12}$ and $R^{13}$ independently represent hydrogen or $C_{1-6}$ alkyl.

3. A compound as claimed in claim 1 represented by formula IIB, or a pharmaceutically acceptable salt or prodrug thereof:

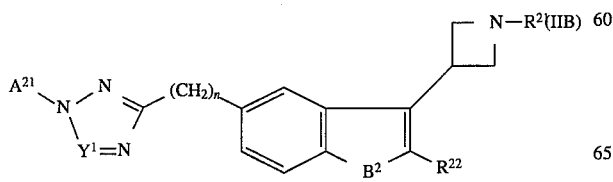

wherein $Y^1$ represents nitrogen or $A^{22}$-C;

n is zero, 1, 2 or 3;

$B^2$ represents oxygen, sulphur or N-$R^{23}$;

$A^{21}$ and $A^{22}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted as defined in claim 1; or hydrogen, halogen, cyano, trifluoromethyl or amino; and $R^{21}$, $R^{22}$ and $R^{23}$ independently represent hydrogen or $C_{1-6}$ alkyl.

4. A compound as claimed in claim 1 represented by formula IIC, or a pharmaceutically acceptable salt or prodrug thereof:

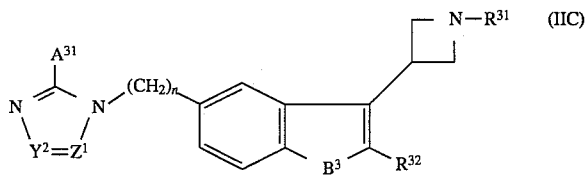

wherein $Y^2$ represents nitrogen or $A^{32}$-C;

$Z^1$ represents nitrogen or CH;

n is zero, 1, 2 or 3;

$B^3$ represents oxygen, sulphur or N-$R^{33}$;

$A^{31}$ and $A^{32}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted as defined in claim 1; or hydrogen, halogen, cyano, trifluoromethyl or amino; and $R^{31}$, $R^{32}$ and $R^{33}$ independently represent hydrogen or $C_{1-6}$ alkyl.

5. A compound as claimed in claim 1 represented by formula IID, or a pharmaceutically acceptable salt or prodrug thereof:

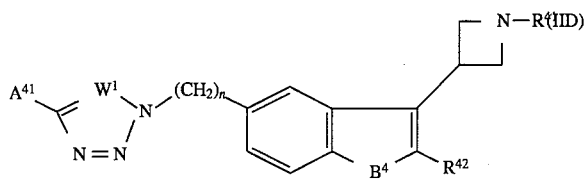

wherein $W^1$ represents nitrogen or C-$A^{42}$;

n is zero, 1, 2 or 3;

$B^4$ represents oxygen, sulphur or N-$R^{43}$;

$A^{41}$ and $A^{42}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted as defined claim 1; or hydrogen, halogen, cyano, trifluoromethyl or amino; and $R^{41}$, $R^{42}$ and $R^{43}$ independently represent hydrogen or $C_{1-6}$ alkyl.

6. A compound as claimed in claim 1 selected from:

N-methyl-3-[5-(2-methylimidazol-1-ylmethyl)-1H-indol-3-yl] azetidine;

N-methyl-3-[5-(1-methyltetrazol-5-ylmethyl)-1H-indol-3-yl] azetidine;

N-methyl-3-[5-(1,2,4-triazol-1-yl)-1H-indol-3-yl] azetidine;

N-methyl-3-[5-(imidazol-1-yl)-1H-indol-3-yl]azetidine;

N-methyl-3-[5-(2-(1-methyltetrazol-5-yl)ethyl)-1H-indol- 3-yl]azetidine;

N-methyl-3-[5-(1,2,4-triazol-1-ylmethyl)-1H-indol-3-yl] azetidine;

N-methyl-3-[5-(1,2,4-triazol-4-yl)-1H-indol-3-yl] azetidine;

N-methyl-3-[5-(imidazol-1-ylmethyl)-1H-indol-3-yl] azetidine;

or a pharmaceutically acceptable salt or prodrug thereof.

7. A pharmaceutical composition comprising a compound as claimed in claim 1 in association with a pharmaceutically acceptable carrier or excipient.

8. A method for the treatment of clinical conditions for which a selective agonist of 5-HT$_1$-like receptors is indicated, which method comprises administering to a patient in need of such treatment an effective amount of a compound of formula I as defined in claim 1, or a pharmaceutically acceptable salt thereof or a prodrug thereof.

* * * * *